(12) United States Patent
Meller

(10) Patent No.: US 7,033,359 B2
(45) Date of Patent: Apr. 25, 2006

(54) ROTARY APPARATUS FOR GRAFTING AND COLLECTING BONE

(76) Inventor: Moshe Meller, 111-Yefa-Nof, Apt 1505, Haifa (IL) 34454

( * ) Notice: Subject to any disclaimer, the term of this patent is extended or adjusted under 35 U.S.C. 154(b) by 118 days.

(21) Appl. No.: 10/667,095

(22) Filed: Sep. 18, 2003

(65) Prior Publication Data

US 2004/0210229 A1 Oct. 21, 2004

Related U.S. Application Data

(60) Provisional application No. 60/464,322, filed on Apr. 21, 2003, provisional application No. 60/471,115, filed on May 16, 2003, provisional application No. 60/498,343, filed on Aug. 26, 2003.

(51) Int. Cl.
*A61B 17/16* (2006.01)

(52) U.S. Cl. .......................... 606/80; 606/102

(58) Field of Classification Search .................. 606/79, 606/80, 102
See application file for complete search history.

(56) References Cited

U.S. PATENT DOCUMENTS

| | | | |
|---|---|---|---|
| 1,493,240 A * | 2/1924 | Bohn | 606/170 |
| 2,525,669 A * | 10/1950 | Hainault | 606/173 |
| 3,308,828 A * | 3/1967 | Pippin | 606/168 |
| 4,706,897 A | 11/1987 | Moeller | |
| 4,844,064 A * | 7/1989 | Thimsen et al. | 606/80 |
| 4,950,296 A | 8/1990 | McIntyre | |
| 5,676,545 A | 10/1997 | Jones | |
| 5,730,372 A | 3/1998 | Bradley | |
| 5,913,859 A * | 6/1999 | Shapira | 606/80 |
| 6,013,077 A | 1/2000 | Harwin | |
| 6,022,354 A | 2/2000 | Mercuri et al. | |
| 6,071,284 A | 6/2000 | Fox | |
| 6,109,916 A | 8/2000 | Wilcko et al. | |
| 6,325,806 B1 | 12/2001 | Fox | |
| 2002/0138078 A1 | 9/2002 | Chappuis | |
| 2003/0158603 A1 | 8/2003 | Ebner | |

* cited by examiner

*Primary Examiner*—Pedro Philogene
(74) *Attorney, Agent, or Firm*—Frishauf, Holtz, Goodman & Chick, P.C.

(57) ABSTRACT

A bone grafter attachment for removing and collecting bone fragments from a donor bone site using a surgical rotational handpiece includes a rotatable drill having a shank engageable with the handpiece and a cutting member, and a container for receiving bone fragments. The container has an opening through which the cutting member passes. The container is held against the donor bone during operation, and the container is held against rotation during rotation of the drill. The drill is axially movable relative to the container to enable the drill to penetrate into the bone. When the drill is rotated by the handpiece and the cutting member thereof engages bone, bone fragments are created and pass over the cutting member and through the opening into the container. Preferably, the cutting member of the drill has flutes through which the bone fragments pass into the container. The collected bone fragments can be removed from the container and used in a bone grafting procedure.

39 Claims, 3 Drawing Sheets

ROTARY APPARATUS FOR GRAFTING AND COLLECTING BONE

REFERENCE TO PROVISIONAL APPLICATIONS

This application claims the benefit of U.S. Provisional Applications Nos. 60/464,322 filed Apr. 21, 2003; 60/471,115 filed May 16, 2003; and 60/498,343 filed Aug. 26, 2003, the entire contents of all of which are incorporated herein by reference.

FIELD OF THE INVENTION

The present invention relates generally to the field of surgery, and more specifically, to apparatus used in connection with Bone Grafting—Bone grafts, which means bone removed from one site and transplanted in another site. The apparatus of the present invention facilitates the removal and collection of bone fragments from a surface of one or more donor sites, e.g. for use in grafting bone to osseous deficiencies, such as periodontal and dentoalveolar defects and bone deficiencies around dental implants. The present invention also relates to methods for removing bone fragments from a surface of bone donor sites and collecting the bone fragments using the apparatus. The invention is not limited to use only in dentistry and dentistry related uses, but may be used to collect bone fragments from any other site in a body for use in any other suitable area of a body. The invention is described below in a non-limiting manner with reference to dental applications for ease of description and understanding.

BACKGROUND OF THE INVENTION

Often, reconstructive procedures used in medicine and dentistry in particular involve the manipulation and healing of bones. Such procedures may involve changes in the position, orientation, shape and size of skeletal structures. A problem that is commonly encountered during such procedures is a lack of a bone graft, e.g., bone from another part of the patient. Bone graft material may be used in several applications, such as to fill between sections of bone that have been repositioned, to change surface geometry, or to add bone to an area that is deficient, such as in conjunction with periodontal surgery or dental implants in the patients' jaws.

Indeed, today, intraoral bone grafting procedures have become an almost integral part of dental implant reconstruction. In many instances, a potential implant site in the upper or lower jaw does not offer enough bone volume or quantity to accommodate a rootform implant of proper size or in the proper place. This may be the result of bone resorption that has taken place since one or more teeth (if not all) were lost. Bone grafting procedures in this case usually try to re-establish bone dimension which was lost due to resorption.

Although there are several materials, both natural and artificial, that can be used for bone grafting, the best material is bone from a donor site of the patient which is removed therefrom and placed somewhere else in the body, i.e., into a recipient site. This is often referred to as an autogenous graft or autograft. The best success rates in bone grafting have typically been achieved when the patient's own bone material is used because the bone is living tissues with their cells intact and there is no immune reaction and the microscopic architecture is matched. For dental implant procedures, bone is often removed from another part of the jaw, i.e., the chin or back portions of the jaw, as an acceptable donor site. This limits the surgery to the mouth and avoids extraoral wounds and scarring.

Clinicians use several techniques to remove bone for grafting for intraoral procedures. In one technique, rotary instruments, such as rotary drills, are used to remove a piece or section of cortical bone from a local intraoral site in the maxilla or mandible. The cortical bone is often morsalized into a particulate form, either manually with a rongeur like instrument or in a bone mill. The particulate bone is then combined with blood to form an osseous coagulum, which is then positioned and packed into the osseous defect around the teeth or implant.

Other techniques for harvesting bone include using chisels to remove shavings from the surface of a bone and enable manual collection thereof. These instruments must be very sharp and the process is often awkward, repetitive and time consuming.

Other manual instruments such as bone files and rasps also remove bone. However, the efficiency of cutting and the ability to use the removed bone is greatly limited. Other known devices use a powered or manual saw which cuts off a part of the bone from a donor site and the cut-off bone then goes through a milling process to create bone fragments.

OBJECTS AND SUMMARY OF THE INVENTION

It is an object of the present invention to provide new and improved apparatus for forming and collecting bone fragments for use in bone grafting procedures, in particular but not limited to, intraoral bone grafting procedures such as dental implant procedures.

It is another object of the present invention to provide a rotary drilling apparatus for removing bone for use in bone grafting procedures that will make the bone grafting procedures easier and faster than the existing procedures.

Another object of the present invention is to provide a rotary drilling apparatus for removing bone for use in bone grafting procedures that can be driven by existing powered surgical motors, such as dental surgical handpieces and the like. In this case, the apparatus is attached to a motor-driven handpiece and the operator is able to hold the handpiece in one hand as with other attachments for the handpiece.

Still another object of the present invention is to provide a rotary drilling apparatus for removing bone for use in bone grafting procedures that is small and simple to fabricate and easy to operate in a patient's mouth.

Yet another object of the present invention is to provide a rotary drilling apparatus for removing bone for use in bone grafting procedures that is disposable.

It is still another object of the invention to provide a new and improved apparatus and method for drilling the jaw bone in preparation for dental implants while simultaneously collecting bone fragments caused by the drilling.

In order to achieve at least one of these objects and others, a bone removing and collecting attachment for a surgical rotational handpiece in accordance with the invention generally comprises a rotatable drill having a shank engageable with the handpiece and a cutting member preferably having spiral flutes, and a container for receiving bone fragments and having an opening through which the cutting member passes. The container is held against rotation during rotation of the drill. The drill is movable relative to the container to enable it to penetrate into the bone. When the drill is rotated by the handpiece and the cutting member thereof engages bone, bone fragments are created and pass over the cutting member and through the opening into the interior of the container. The collected bone fragments can later be removed from the container and used in a bone grafting procedure.

When the drill has spiral flutes, the spiral flutes push the created bone fragments up and into the interior of the container.

A bone removal and collecting procedure in accordance with the invention thus involves the use of a surgical dental handpiece, which is easy to use and which is found in almost every medical and dental facility, and is much less time-consuming than the use of a chisel, thus reducing or eliminating operator fatigue.

In one embodiment, the cutting member is a drill bit including one or more flutes through which bone fragments pass into the container. The drill bit can be used to drill into the jaw bone of a patient to form an implant site so that at the same time, the implant site is created and bone fragments which may be needed during the implant procedure are obtained.

When the cutting member is a drill bit, the container can comprise an inner sleeve unit having at least one peripheral opening and an outer sleeve surrounding part of the inner sleeve unit. The outer sleeve is selectively fixed to the inner sleeve unit, i.e., it is removably coupled thereto to enable separation of the outer sleeve unit from the inner sleeve and thus access to the bone fragments which have been collected in the interior of the container. The outer sleeve may be transparent so that it is possible to see when the container is full of bone fragments and needs to be emptied. The inner sleeve unit may include an inner sleeve defining the peripheral opening(s) and an annular bottom part coupled thereto and defining the opening through which the cutting member passes. The inner and outer sleeve can rest on the annular bottom part and be fixed together by a pin mounted on the annular bottom part. In this manner, when the outer sleeve is prevented from rotating, the inner sleeve unit is also prevented from rotating.

A pressing mechanism may be provided to urge the container to cover the cutting member and ensure that bone fragments collected in the container are retained therein. In one embodiment, the pressing mechanism includes a spring holder arranged around and movable relative to the shank, a compression spring arranged between the spring holder and the container and a locking spring ring fixed to the shank. The spring holder is urged by the spring against the locking spring ring.

To prevent rotation of the container upon rotation of the drill, a rod may be attached to the container, e.g., the outer sleeve thereof, and adapted to engage the handpiece upon rotation thereof so that once the rod contacts the handpiece, further rotation of the container is prevented.

Instead of opening the container, the container can be emptied by operating the drill bit in reverse by operating the surgical dental handpiece in reverse. This causes the fragments in the container to be ejected from the container by action of the flutes in the drill bit. This operation should remove most of the bone fragments in the container. The container can be opened as described above to remove the remainder of the bone fragments, if desired.

Instead of the multi-sleeve container described above, another type of container can be provided which is manually held against rotation. To this end, the attachment includes a handle adapted to be operatively held by an operator and the container is removably coupled to the handle, e.g., by cooperating threads. The container is held by one hand of the operator while the handpiece is held by the operator's other hand. When the container is full, which may be readily determined if the container is made of a transparent material, the handle is disconnected from the container to thereby open the container and allow access to the bone fragments collected in the container.

As indicated above, the fragments can be removed from the container by operating the drill bit in reverse. If fragments remain in the container, the remaining fragments can be removed by opening the container, as described above.

Instead of a drill bit, the cutting member may be a milling cutter having cutting blades on a bottom planar surface and on a side cylindrical surface. This enables milling in either a direction perpendicular to the surface of the bone or in a direction parallel to the surface of the bone. Preferably, the milling cutter has spiral flutes arranged at an angle from about 30° to about 75° relative to the bottom planar surface to provide for a steady flow of bone fragments through the flutes into the container (and out of the container when the drill bit is rotated in reverse).

When the cutting member is a milling cutter, the container may have a different form than described above. Specifically, the container may comprise a cylindrical sleeve, an annular bottom part removably coupled to the sleeve and defining the opening in which the milling cutter is arranged, an annular top part coupled to or integral with the sleeve and an upper guide ring arranged in an opening defined by the top part. The upper guide ring defines an opening through which a portion of the drill passes. To provide for the removable coupling between the bottom part and the sleeve to enable access to the interior of the container in which the bone fragments are collected, the sleeve and the annular bottom part include cooperating threads.

In this embodiment, to prevent rotation of the container upon rotation of the drill, a projecting arm may be provided extending outward from the sleeve and include a groove and an elastic ring provided to extend around the handpiece arm and in the groove. In view of a pre-determined limit on its expansion, the elastic ring prevents rotation of the container. A rigid arm as described previously hereinablve could be used in place of an elastic ring.

BRIEF DESCRIPTION OF THE DRAWINGS

The invention, together with further objects and advantages thereof, may best be understood by reference to the following description taken in conjunction with the accompanying drawings, wherein like reference numerals identify like elements.

DETAILED DESCRIPTION OF THE INVENTION

Figure 1:
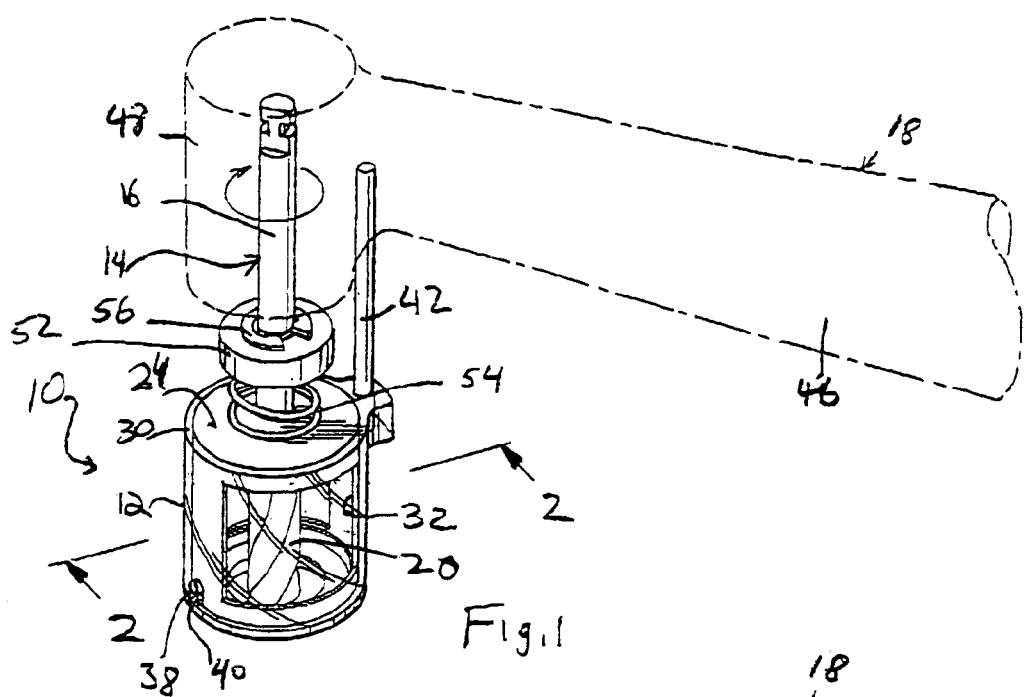
FIG. 1 is a perspective view of a first embodiment of a bone grafter attachment for a rotary handpiece in accordance with the invention showing the handpiece in phantom lines.

Referring first to FIGS. 1–4, a first embodiment of a bone grafter and bone fragment collection attachment (herein after referred to as a "bone grafter attachment") for use with a surgical rotational dental-type handpiece is designated generally as 10. The bone grafter attachment unit 10 includes a container 12 for receiving bone fragments and a rotatable drill 14 having a shank 16 engageable with the handpiece 18 and a cutting member, such as a drill bit 20. The drill bit 20 passes through an opening 22 in a bottom of the container 12 and is movable relative to the container 12 (see FIG. 2). The drill bit 20 is made of a surgical steel capable of drilling bone.

The end of the shank 16 which engages with the handpiece 18 has the appropriate mating connection for the specific surgical handpiece 18. Thus, a different bone grafter attachment unit 10 can be produced for each handpiece having a particular mating connection and the bone grafter attachment unit 10 would then be connected to the handpiece in the usual manner of connecting attachments to that handpiece (most of the handpieces, however, have standard connections).

The container 12 includes an inner sleeve unit 24 made of a cylindrical inner sleeve 26 (having openings 32 therein) and an annular bottom part 28 which defines the opening 22, and a cylindrical outer sleeve 30 surrounding the inner sleeve 26. The inner sleeve 26 includes two peripheral openings 32 which enable bone fragments which have been collected in the container 12 to be removed therefrom. The annular bottom part 28 includes a circumferential lip 34 on which the inner sleeve 26 and the outer sleeve 30 rest. Although the Inner sleeve 26 is shown as a separate part from the annular bottom part 28, the inner sleeve unit 24 and bottom part 28 can be an integral unit having the opening 22 through which the drill bit passes (and through which bone fragments enter into the container 12) and one or more peripheral openings 32 through which the bone fragments can be removed from the container 12, i.e., when the outer sleeve 30 is moved to expose the peripheral openings 32. Otherwise, when the outer sleeve 30 surrounds the inner sleeve 26, it covers the peripheral openings 32. The opening 22 may have a slightly larger diameter than the diameter of the drill bit to provide a small clearance for bone fragments. The inner sleeve 26 and bottom part 28 may be made of stainless steel with an aperture 26a in the top part through which the drill shank 16 passes so as to hold and guide the drill 14.

A resilient cover may be arranged, if desired, on the bottom surface of the annular bottom part 28 and adapted to engage the bone.

The outer sleeve 30 may be made of a clear, transparent material to enable the volume of bone fragments in the container 12 to be visually ascertained by the operation during use of the bone grafter attachment unit 10. This would allow the bone removal and collection procedure to be stopped once a sufficient amount of bone fragments are determined to be present in the container 12 or when the container 12 is determined to be full.

A pin 38 is fixed relative to the inner sleeve unit 24 and to bottom part 28 and projects radially outward from the inner sleeve 26. The outer sleeve 30 includes an axially extending slot 40 (see FIGS. 1 and 4) so that when the outer sleeve 30 is slid down over the inner sleeve 26 with the pin 38 situated in the slot 40, the outer sleeve 30 is fixed to the inner sleeve unit 24 and rests on the outwardly projecting part 28. That is, the inner sleeve unit 24 and outer sleeve 30 rotate or remain stationary together. The outer sleeve 30 is movable relative to the inner sleeve unit 24 by sliding the outer sleeve 30 upward in an axial direction so that the pin 38 is no longer present in the slot 40. In this position, the peripheral openings 32 are exposed thereby enabling removal of bone fragments from the container 12. Instead of moving the outer sleeve 30 relative to the inner sleeve unit 24, the inner sleeve unit 24 can be moved axially downward relative to the outer sleeve 30 with the same effect. Other mechanisms for selectively fixing the outer sleeve 30 and the inner sleeve unit 24 together can also be used in the invention.

Since the drill 14 is rotated relative to the container 12, this causes an upward flow of grafted material (bone fragments) into the container 12 during operation of the bone grafter attachment unit 10.

Figure 2:
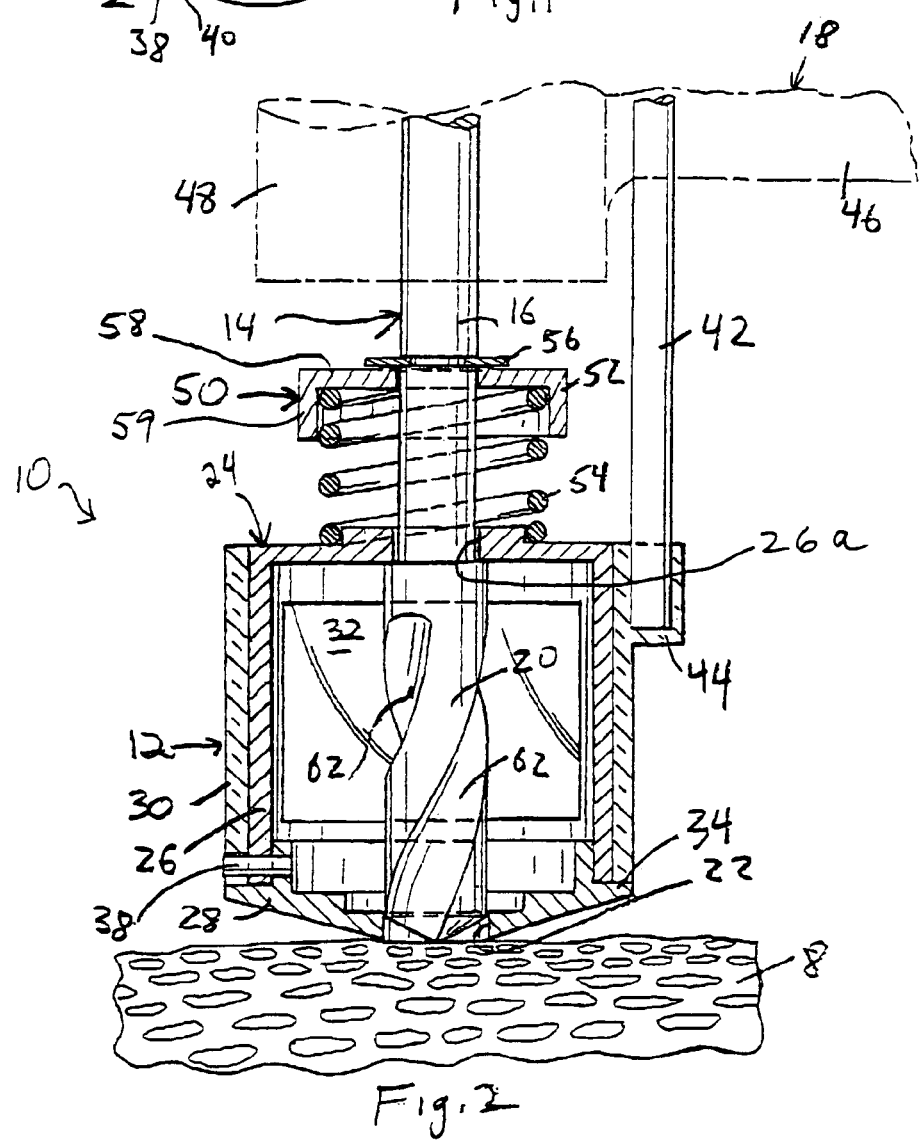
FIG. 2 is a cross-section taken along the line 2—2 of FIG. 1 with the bone grafter attachment being shown in preparation for use.
Figure 3:
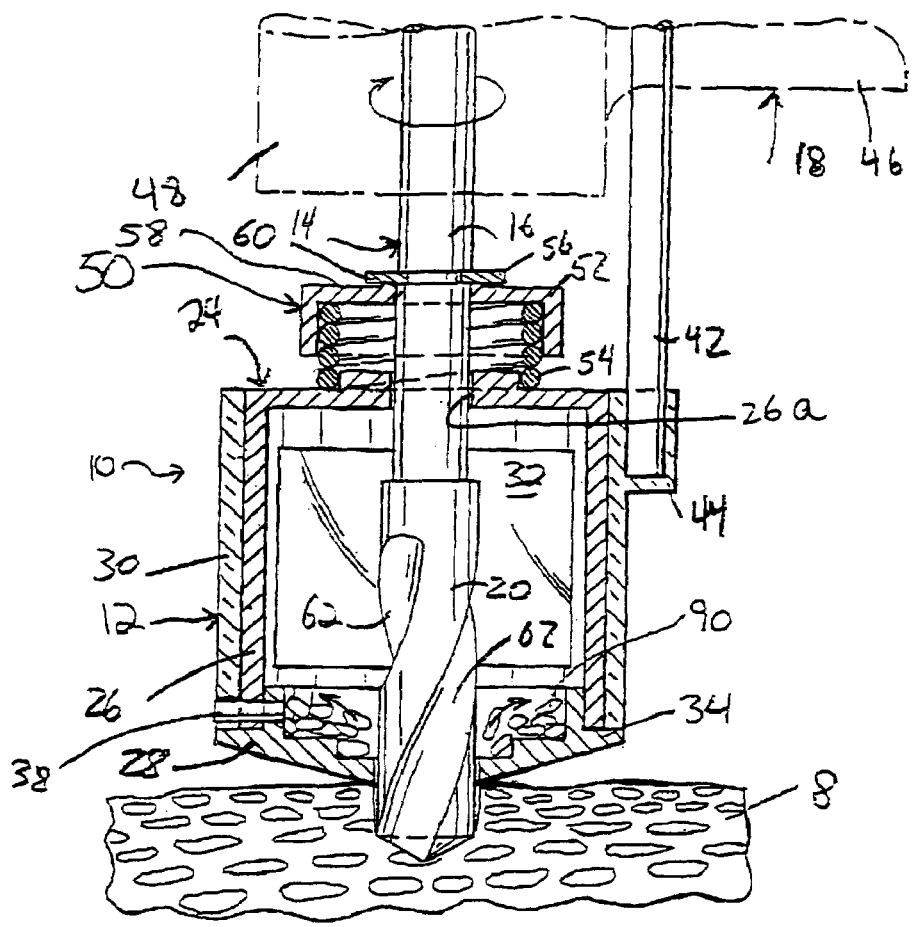
FIG. 3 is a cross-section taken along the line 2—2 of FIG. 1 with the bone grafter attachment being shown during use.
Figure 4:
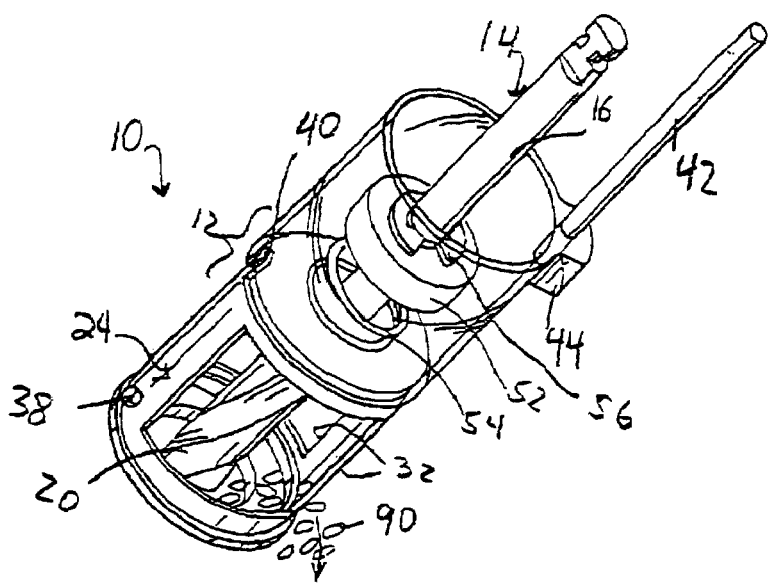
FIG. 4 is a perspective view of the bone grafter attachment showing the manner in which bone fragments are removed therefrom.

Since the drill 14 is rotated, it is desirable to hold the container 12 against rotation so that the relative rotational motion between drill bit 62 and the lower portion 28 of the container 12 produces the flow of grafted material into the container 12. To this end, a mechanism is provided to prevent rotation of the container 12 upon rotation of the drill 14. Specifically, the mechanism comprises an elongate rod 42 attached to the container 12 and adapted to engage the handpiece 18 as shown in FIGS. 1–3. The rod 42 is connected to a flange or projection 44 formed on the outer sleeve 30 (see FIG. 1). Rod 42 may be made of stainless steel and may be secured in an opening of the projection 44 by press fit or by an adhesive.

The height of the rod 42 is sufficient to contact the arm 46 of the handpiece 18 so that a complete rotation of the container 12 around the head 48 of the handpiece 18 is precluded. It is noted though that depending on the position of the rod 42 when the bone grafter attachment unit 10 is connected to the handpiece 18, the container 12 may rotate until the rod 42 contacts the handpiece arm 48. However, once contact is established between the rod 42 and the handpiece arm 48, further rotation of the container 12 is prevented. Moreover, separation of the container 12 from the drill 14 is prevented by a shoulder formed between the drill bit 20 and the shank 16 and which is situated in an interior of the contaier 12. This shoulder has an upper, extreme position abutting against the inner sleeve 26 to thereby prevent the container 12 from sliding off of the drill 14 (see FIG. 2).

Prior to use of the bone grafter attachment unit 10, the drill bit 20 should be situated within the container 12, i.e., the container should surround the drill bit 20. In addition, during use, it is desirable to keep the container 12 against the bone 8 while allowing movement of the drill 20 relative to the bone 8. To this end, a pressing mechanism 50 is provided to urge the container 12 against the bone 8 during use (and maintain the container against the bone 8 during use) and to cover the drill bit 20 during non-use. In the illustrated embodiment of FIGS. 1–4, the container 12 would be urged downward such that the annular bottom part 28 contacts the bone 8 and no portion of the drill bit 20 is exposed (see FIG. 2).

The pressing mechanism 50 comprises a spring holder 52 arranged around and movable relative to the drill shank 16, a compression spring 54 arranged between the spring holder 52 and an upper part of the container 12 and a locking spring ring 56 fixed to the drill shank 16. The spring holder 52 is urged by the spring 54 against the locking spring ring 56 at one end of the spring 54 whereas the other end of the spring 54 urges the container 12 down to cover the drill bit 20. The spring holder 52 has a planar annular portion 58 defining an opening 60 through which the shank 16 passes and a cylindrical side portion 59 extending outward of the spring 54.

Thus, in operation with the pressing mechanism, the drill bit 20 is movable into and out of the bone 8 while the annular bottom part 28 is continuously pressed (urged) against the bone 8. Movement of the drill bit 20 relative to the bone 8 and relative to opening 22 enhances the flow of bone fragments into the container 12.

In use, the bone grafter attachment unit 10 in the position shown in FIG. 1 is initially connected to the handpiece 18. The motor of the handpiece 18 is initiated in the usual manner and the drill bit 20 starts to rotate. The handpiece 18 with the bone grafter attachment unit 10 connected thereto is moved over the bone donor site. The handpiece 18 is then moved toward the bone 8 causing the annular bottom part 28 to contact the bone 8 and then upon further movement of the handpiece 18 toward the bone 8, the drill bit 20 is caused to engage the bone 8 and drills into the bone 8 to form bone fragments. The bone fragments pass through the flutes 62 in the drill bit 20 into an interior of the container defined by the inner sleeve unit 24 and the outer sleeve 30. During this time, the container 12 is moved relative to the drill bit 20 against the bias of the spring 54 (by means of which the container remains pressed against the bone 8 as shown in FIGS. 2 and 3). Pressing of the container 12 against the bone 8 under the influence of spring 54 also prevents bone fragments from escaping enables positive guiding of the generated bone fragments into the container 12. Further pressing of the handpiece 18 toward the bone (and removal and collection of bone fragments in the container 12) is permitted until the spring 54 is compressed to its fullest extent (as shown in FIG. 3). This also limits the depth of penetration of the drill bit into the bone to a safe depth.

By viewing the quantity of bone fragments in the container 12 through the transparent outer sleeve 30, a determination can be made as to when the container 12 is full. At this time, the handpiece 18 is moved away from the bone 8, and out of the patient's mouth if the donor site is in the patient's mouth. The bone grafter attachment unit 10 is disconnected from the handpiece 18 in the usual manner that attachments for that handpiece are disconnected therefrom.

The bone grafter attachment unit 10 would then be placed over a receptacle and the outer sleeve 30 and inner sleeve unit 24 axially separated from one another to expose the peripheral openings 32 in the inner sleeve 26. The bone fragments which were collected in the container 12 would then fall out of the container 12 and into the receptacle (see FIG. 4). The bone removal and collection procedure could continue by axially sliding the outer sleeve 30 over the inner sleeve unit 24, reattaching the bone grafter attachment unit 10 to the handpiece 18 and proceeding in the same manner as described above.

Once the container 12 is opened for removal of the bone fragments, the bone fragments can be pushed out of the container into a receptacle by using an instrument. It is also not necessary to disconnect the bone grafter attachment unit 10 from the handpiece 18 in order to empty same. The bone grafter attachment 10 can remain on the handpiece 18 during emptying so that it can be in proper position for carrying out a second bone fragment collection process.

Still further, instead of opening the container by moving the outer sleeve 30 relative to the inner sleeve unit 24, the bone grafter attachment unit can be emptied of bone fragments by placing same over a receptacle or the like, and then operating the drill 20 in reverse. This causes bone fragments in the container to pass out of the container through the flutes 62 in the drill bit 20, thus facilitating emptying of the container. Any bone fragments remaining in the container after operating the drill bit in reverse (by operating the handpiece in reverse) can be removed by opening the container by sliding the outer sleeve 30 relative to the inner sleeve unit 20, as discussed above.

Non-rotational coupling between the inner sleeve unit 24 and the outer sleeve 30 can be achieved by making the inner and outer sleeves non-circular in shape. In such case, when the outer sleeve 30 is engaged over the inner sleeve unit 24, and the shapes are matching non-circular shapes, the outer sleeve 30 will be non-rotational relative to the inner sleeve unit 24. This eliminates the need for the pin 38 and slot 40 shown in FIGS. 1–4. For example, the inner and outer sleeves can be oval, rectangular or any other non-circular shape. Other non-rotational coupling techniques between the inner and outer sleeves can be used. For example, the inner sleeve could have a projection thereon, and the outer sleeve could have a recess which mates with the projection (and vice versa) to non-rotationally couple the inner and outer sleeves together. Other non-rotational coupling techniques could be used, as desired.

Figure 5:
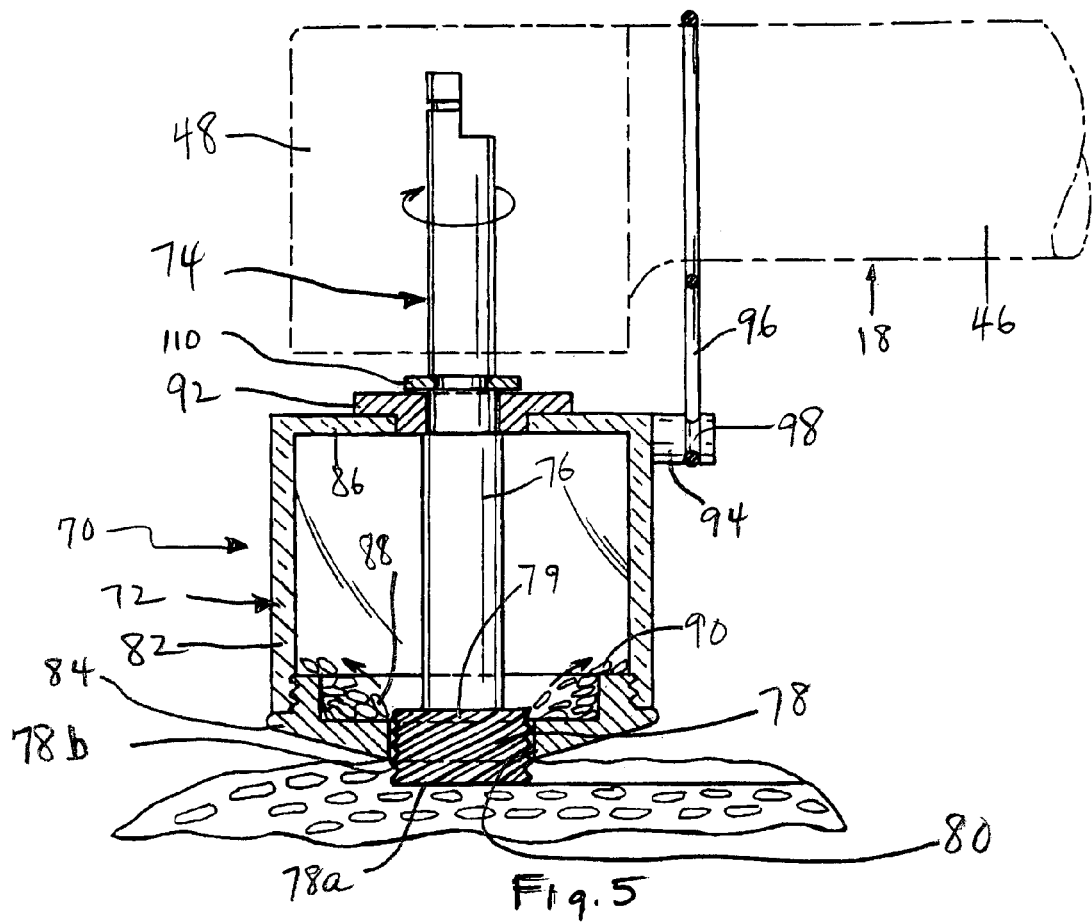
FIG. 5 is a cross-section of a second embodiment of a bone grafter attachment for a rotary handpiece in accordance with the invention showing the handpiece in phantom lines.

Referring now to FIG. 5, a second embodiment of a bone grafter attachment unit for a surgical handpiece is designated generally as 70. The bone grafter attachment unit 70 includes a container 72 for receiving bone fragments and a rotatable drill 74 having a shank 76 engageable with the handpiece 18 and a cylindrical milling cutter 78. The milling cutter 78 is not shown in cross-section. The milling cutter 78 has cutting blades on its bottom surface 78a and on its side surface 78b and is arranged in an opening 80 in a bottom of the container 72. The opening 80 thus typically is provided with a slightly larger diameter than the diameter of the milling cutter 78 to provide a small clearance for bone fragments. The milling cutter 78 is made of a surgical steel capable of milling bone.

In a preferred embodiment, the milling cutter 78 has spiral flutes 79 on the side thereof, which flutes 79 are arranged at an angle from about 30° to about 75° relative to the bottom and top planar surfaces of the milling cutter 78. These angles improve the flow of bone fragments from the bone 8 into the container 72 through the flutes 79.

The end of the shank 76 which engages with the handpiece 18 has the appropriate mating connection for the specific surgical handpiece 18. Thus, a different bone grafter attachment unit 70 can be produced for each handpiece having a particular mating connection and the bone grafter attachment unit 70 would then be connected to the handpiece in the usual manner of connecting attachments to that handpiece.

The container 72 includes a cylindrical sleeve 82, an annular bottom part 84 removably coupled to the sleeve 82 and a top part 86 which may be integral with the sleeve 82. The annular bottom part 84 defines the opening 80 in which the milling cutter 78 is arranged. The annular bottom part 84 can also include an internal shoulder 88 adapted to operatively receive bone fragments 90. An upper guide ring 92 is arranged in an opening defined by the top part 86 and itself defines an opening through which a portion of the shaft of the drill 74 passes.

In the illustrated embodiment, the sleeve 82 and the annular bottom part 84 are provided with cooperating threads to enable the removable coupling therebetween. Other mechanisms for removably coupling the sleeve 82 to the annular bottom part 84 are also envisioned, such as the mechanism shown in FIGS. 1–4.

The sleeve 82 may be made of a clear, transparent material to enable the volume of bone fragments in the container 72 to be visually ascertained during use of the bone grafter attachment. This would allow the bone removal and collection procedure to be stopped once a sufficient amount of bone fragments are determined to be present in the container 72 or the container 72 is determined to be full.

Since the drill 74 is rotated, it is desirable to hold the container 72 against rotation. To this end, a mechanism is provided to prevent rotation of the container 72 upon rotation of the drill 74. In this embodiment, the mechanism comprises a projecting arm 94 extending radially outward from the sleeve 82 and an elastic ring 96. The projecting arm 94 may be integral with the sleeve 82 or separated therefrom and fixed thereto. The elastic ring 96 is operatively extended around the handpiece arm 48 and in a groove 98 on the projecting arm 94. Instead, the rigid elongated rod or pin 42 of FIGS. 1–4 may be used to hold the container 72 against rotation, as shold readily be apparent.

The elasticity of the ring 96 is selected to enable the ring 96 to pass over the head of the handpiece 18 during connection of the bone grafter attachment 70 to the handpiece 18 yet serve to prevent rotation of the container 72 around the head of the handpiece 18. The elasticity of the ring 96 also allows axial movement of the container 72 relative to the drill 74. It is noted though that some rotation of the container 72 relative to the handpiece 18 is likely until a point at which the ring 96 has reaches its maximum expansion and further expansion is not possible.

The bone grafter attachment unit 70 includes a mechanism for limiting the relative axial movement between the milling cutter 78 and the container 72. This mechanism is necessary to ensure that the milling cutter 78 is not entirely outside of the container 72, in which case, the bone fragments would not pass into the container 72. The mechanism comprises an annular ring 100 attached to the shaft of the drill 74.

In use, the bone grafter attachment unit 70 is initially connected to the handpiece 18 and the rubber ring 96 is placed over the head of the handpiece 18 and into the groove 98. The motor of the handpiece 18 is initiated in the usual manner and the drill shaft 74 and milling cutter 78 thereof start to rotate. The handpiece 18 with the bone grafter attachment unit 70 connected thereto is moved over the bone donor site, either in a lateral direction or perpendicular direction to the surface of the bone, such that the milling cutter 78 contacts the bone 8. The container 72 is pressed downward to contact the bone, as shown in FIG. 5. Upon the rotation of the milling cutter 78, the blades of the milling cutter 78 cut the bone and create bone fragments which pass along the spiral flutes between side cutting blades 78b on the side of the milling cutter 78 into the container 72.

Although the shank 76 is journalled by the top part 86 of the container 72, friction may be created which would cause rotation of the container 72. This rotation is limited by the elasticity of the rubber ring 96.

By viewing the quantity of bone fragments in the container 12 through the transparent sleeve 82, a determination can be made as to when the container 72 is full. At this time, the handpiece 18 is moved away from the bone 8, and out of the patient's mouth if the donor site is in the patient's mouth. The bone grafter attachment 70 is disconnected from the handpiece 18, in the usual manner that attachments for that handpiece are disconnected therefrom. The bone grafter attachment unit 70 would then be placed over a receptacle and the annular bottom part 84 unscrewed from the sleeve 82 to allow the bone fragments which were collected in the container 72 to fall out of the container 72 and into the receptacle. The bone fragment removal (by opening the container) can be done without detaching the bone grafter attachment unit 70 from the handpiece 18. The bone removal and collection procedure could continue by re-screwing the annular bottom part 84 to the sleeve 82, reattaching the bone grafter attachment unit 70 to the handpiece 18 (if they were detached during emptying) and proceeding in the same manner as described above.

As should be readily apparent, the container unit 72 of the embodiment of FIG. 5 can be replaced with a container unit substantially the same as the container unit 12 of FIGS. 1–4. That is, the inner and outer sleeves of FIGS. 1–4 could be used in the embodiment of FIG. 5. Still further, the pressing mechanism 50 of FIGS. 1–4 could be used in the embodiment of FIG. 5, to positively urge the container 72 toward the bone during use of the device to prevent bone fragments from scattering.

While a coil spring 54 is shown in the embodiment of FIGS. 1–4, other types of spring units could be used, for example such as a bellows springy member, a highly yieldable block of rubber-like material, a resilient material, etc.

Figure 6:
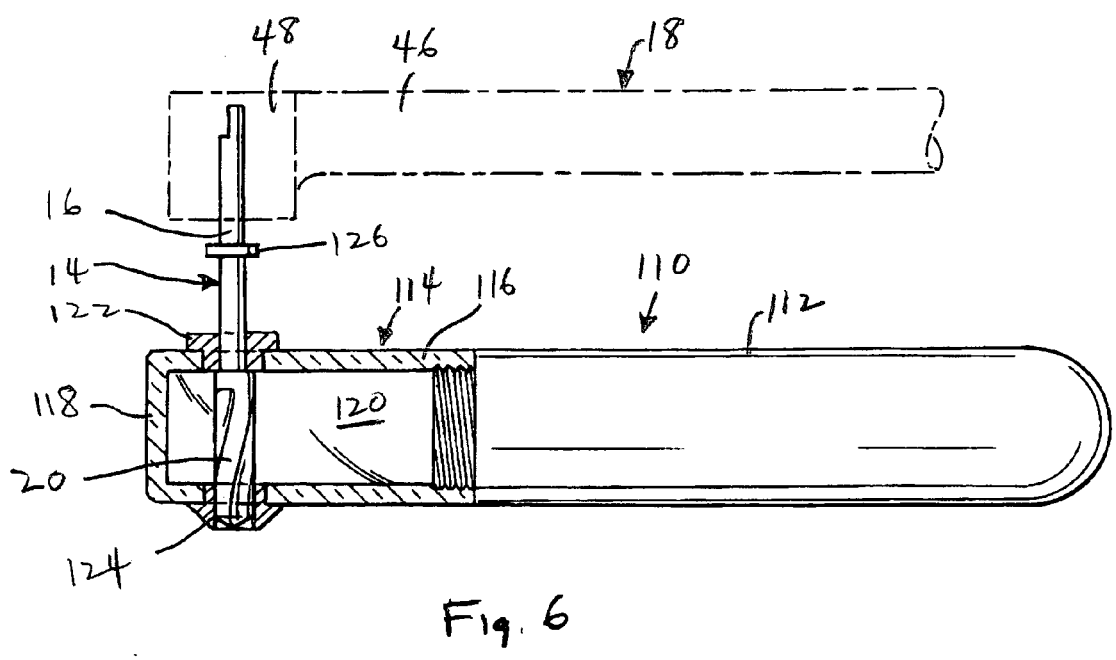
FIG. 6 is a partial cross-section of a third embodiment of a bone grafter attachment for a rotary handpiece in accordance with the invention showing the handpiece in phantom lines.

Referring now to FIG. 6, another embodiment of a bone grafter attachment unit for a surgical handpiece is designated generally as 110. The bone grafter attachment 110 includes a handle 112 designed to be grasped by an operator's hand, a container 114 for receiving bone fragments removably coupled to the handle 112, and a rotatable drill 14 having a shank 16 engageable with the handpiece 18 and a drill bit 20. The end of the shank 16 which engages with the handpiece 18 has the appropriate mating connection for the specific surgical handpiece 18.

To provide for the removable coupling, the handle 112 and the container 114 are provided with cooperating threads, although other removable coupling mechanisms could be used in the invention. The handle 112 and container 114 have a cylindrical shape in the illustrated embodiment but can be provided with other cross-sectional shapes. At least a portion of the handle 112 would typically be provided with a contour amenable to handling by an operator as the attachment is preferably hand-held during use.

The container 114 has a tubular sleeve 116 which is oriented in the same direction as the handpiece 18, i.e., horizontal in the illustrated embodiment, and which is closed by an end wall 118 which may be coupled to or integral with the sleeve 116 to thereby define a closeable interior 120 in which bone fragments are operatively received. The container 114 is preferably made of a transparent material to enable viewing of the contents of the interior 120. The handle 112 may be made of plastic.

An upper drill guide 122 is fitted in an opening in an upper side of the sleeve 116 and a lower drill guide 124 is fitted in an opening in a lower side of the sleeve 116. The upper and lower drill guides 122, 124 may be made of stainless steel or another material compatible for contact with human tissue and bone. Since the lower drill guide 124 rests on the bone as the drill bit 20 engages the bone 8, the lower drill guide 124 has a conical shape which permits secure engagement with the surface of the bone 8.

The bone grafter attachment 110 includes a mechanism for limiting the relative axial movement between the drill 14 and the container 114. This mechanism is necessary to ensure that the drill bit 20 is not entirely outside of the container 114, in which case, the bone fragments would not pass into the container 114 and would scatter. The mechanism comprises an annular ring 126 attached to the shank 16 of the drill 14. A pressing mechanism, such as the mechanism 50 of FIGS. 1–4, may also be provided to provide positive and automatic urging engagement of the lower drill guide 124 against the bone during use.

In use, the bone grafter attachment unit 110 is initially connected to the handpiece 18 via the shank 16. The motor of the handpiece 18 is initiated in the usual manner and the drill bit 20 starts to rotate. The handpiece 18 is held with one hand and the bone grafter attachment 110 is held by the other and the drill bit 20 is moved over the bone donor site. The handpiece 18 is then moved toward the bone 8 causing the lower drill guide 124 to contact the bone 8 and then upon further movement of the handpiece 18 toward the bone 8, the drill bit 20 is contacts the bone 8 and drills the bone 8 to form bone fragments. The bone grafter attachment 110 may be manually pused against the bone by the operator. The bone fragments pass through the flutes 62 in the drill bit 20 into the interior 120 of the container 114. During this time, the drill bit 20 is moved toward the bone 8 and relative to the container 114. This movement is limited by the annular ring 126 which also limits the depth of penetration into the bone.

By viewing the quantity of bone fragments in the container 114, a determination can be made to when the container 114 is full. At this time, the handpiece 18 is moved away from the bone 8, and out of the patient's mouth if the donor site is in the patient's mouth. The container 114 is unscrewed from the handle 112 when over a receptacle so that the bone fragments in the container 114 fall into the receptacle. Although not required to remove the bone fragments from the interior 120 of the container 114, it is possible to disconnect the bone grafter attachment 110 from the handpiece 18 by separating the shank 16 from the handpiece 18 in the usual manner that attachments 110 for that handpiece 18 are disconnected therefrom. The bone removal and collection procedure could continue by re-screwing the handle 112 and container 114 together, reattaching the attachment 110 to the handpiece 18 (if it was separated therefrom) and proceeding in the same manner as described above. As indicated above, the container 114 can be emptied by operating the drill bit in reverse so as to feed the bone fragments in the container through the flutes and out of the container, into a receptacle or the like. If any bone fragments remain in the container 114 after this procedure, it may completely emptied by unscrewing the container 114 from the handle 112, as described hereinabove.

It should be clear that various other modifications and alterations can be made within the scope of the present invention. Also, various features of one embodiment can be combined with features of other embodiments, consistent with proper operation thereof, within the scope of the present invention.

I claim:

1. A bone grafter attachment unit for removing and collecting bone fragments from a bone, using a surgical rotational handpiece, the bone grafter attachment unit comprising:
   a rotatable drill having a shank engageable with the handpiece, and a cutting member; and
   a container for receiving bone fragments and having an opening at a bottom through which said cutting member passes, said container being held against rotation during rotation of said drill and said drill being movable relative to said container,
   said container comprising an inner sleeve unit having at least one peripheral opening along a side and an outer sleeve surrounding at least a part of said inner sleeve unit, said outer sleeve being selectively fixed to said inner sleeve unit such that when said outer sleeve is fixed to said inner sleeve unit, said at least one peripheral ooenino is covered by said outer sleeve,
   whereby when said drill is rotated by the handpiece and said cutting member engages bone, bone fragments are created and pass over said cutting member and through said opening in the bottom of said container into said container.

2. The bone grafter attachment unit of claim 1, wherein said cutting member comprises a drill bit having flutes through which said bone fragments pass into said container.

3. The bone grafter attachment of claim 1, further comprising an engagement mechanism for engaging said inner sleeve unit and said outer sleeve together to prevent any relative rotation between said inner sleeve unit and said outer sleeve.

4. The bone grafter attachment unit of claim 1, wherein said outer sleeve is transparent.

5. The bone grafter attachment unit of claim 1, further comprising a fixing device coupled to at least one of said outer sleeve and inner sleeve unit for selectively fixing said outer sleeve to said inner sleeve unit.

6. The bone grafter attachment unit of claim 5, wherein said fixing device comprises a pin fixed to said inner sleeve unit, said outer sleeve including a slot receivable of said pin whereby when said pin is received in said slot, said outer sleeve is fixed to said inner sleeve unit and by sliding said outer sleeve until said pin is removed from said slot, said outer sleeve is movable relative to said inner sleeve unit and said at least one peripheral opening is exposed.

7. The bone grafter attachment unit of claim 6, wherein said slot is arranged in an axial direction of said container.

8. The bone grafter attachment unit of claim 1, wherein said inner sleeve unit comprises an inner sleeve portion defining said at least one peripheral opening, and an annular bottom part coupled to said inner sleeve portion, said annular bottom part defining said opening in the bottom of said container through which said cutting member passes.

9. The bone grafter attachment unit of claim 8, wherein said annular bottom part includes a circumferential lip, said inner sleeve portion and said outer sleeve engaging said circumferential lip.

10. The bone grafter attachment unit of claim 1, further comprising a pressing unit for urging said container to cover said cutting member.

11. The bone grafter attachment unit of claim 10, wherein said pressing unit comprises:
    a spring holder arranged around and movable relative to said shank;
    a spring member arranged between said spring holder and said container; and
    a locking spring ring fixed to said shank, said spring holder being urged by said spring member against said locking spring ring.

12. The bone grafter attachment unit of claim 11, wherein said spring member comprises a compression coil spring.

13. The bone grafter attachment unit of claim 11, wherein said spring holder has a planar annular portion defining an opening through which said shank passes and a cylindrical side portions extending outward of said spring member.

14. The bone grafter attachment unit of claim 1, further comprising a rotation preventing mechanism for preventing rotation of at least part of said container upon rotation of said drill.

15. The bone grafter attachment unit of claim 14, wherein said rotation preventing mechanism comprises an arm attached to said container and adapted to engage the handpiece.

16. The bone grafter attachment unit of claim 15, wherein said arm is attached to said outer sleeve such that rotation of said outer sleeve upon rotation of said drill is prevented.

17. The bone grafter attachment unit of claim 16, wherein said container further comprises a pin fixed to said inner sleeve unit, said outer sleeve including a slot arranged in an axial direction of said container and receivable of said pin whereby when said pin is received in said slot, said outer sleeve is fixed to said inner sleeve unit and rotation of said inner sleeve unit upon rotation of said drill is prevented, said outer sleeve being movable relative to said inner sleeve unit to expose said at least one peripheral opening by sliding said outer sleeve until said pin is removed from said slot.

18. The bone grafter attachment unit of claim 1, wherein said cutting member includes at least one flute for enabling bone fragments to pass into said container.

19. The bone grafter attachment unit of claim 1, wherein said cutting member comprises a milling cutter having cutting blades on a bottom planar surface and on a side cylindrical surface thereof.

20. The bone grafter attachment unit of claim 19, wherein said milling cutter has spiral flutes on a side surface thereof, said flutes being arranged at an angle from about 30° to about 75° relative to said bottom planar surface.

21. The bone grafter attachment unit of claim 1, wherein said inner sleeve unit comprises a inner, substantially cylindrical sleeve, and an annular bottom part removably coupled to said inner sleeve and defining said opening in the bottom of said container through which said cutting member passes.

22. The bone grafter attachment unit of claim 21, wherein said container further comprises:
an annular top part coupled to or integral with said inner sleeve; and
an upper guide ring arranged in an opening defined by said top part, said upper guide ring defining an opening through which a portion of said drill passes.

23. The bone grafter attachment unit of claim 21, wherein said inner sleeve and said annular bottom part include cooperating threads.

24. The bone grafter attachment unit of claim 21, further comprising a rotation preventing mechanism for preventing rotation of said container upon rotation of said drill.

25. The bone grafter attachment unit of claim 24, wherein said rotation preventing mechanism comprises:
a projecting arm extending outward from said inner sleeve and including a groove; and
an elastic ring adapted to be extended around the handpiece arm and in said groove.

26. The bone grafter attachment unit of claim 25 further comprising an annular ring fixed to said drill for limiting axial movement of said container upon contraction of said elastic ring.

27. The bone grafter attachment unit of claim 1, further comprising a handle adapted to be operatively held by an operator, said container being removably coupled to said handle.

28. The bone grafter attachment unit of claim 27, wherein said container and said handle include cooperating threads which enable removable coupling of said container to said handle.

29. The bone grafter attachment unit of claim 27, wherein said container includes:
an upper drill guide fitted in an opening in an upper side of said container; and
a lower drill guide fitted in an opening in a lower side of said container, said upper and lower drill guides each including an opening through which said drill passes.

30. The bone grafter attachment unit of claim 27, further comprising an annular ring fixed to said drill for limiting movement of said drill into the bone.

31. A system for removing and collecting bone fragments from a bone, comprising:
a surgical rotational handpiece having a forward and a reverse rotational motion; and
a bone grafter attachment unit attached to said handpiece, said bone grafter attachment unit comprising:
a rotatable drill having a shank engaged with said handpiece and a cutting member;
a container for receiving bone fragments and having an opening through which said drill passes, said container being held against rotation during rotation of said drill and said drill being movable relative to said container; and
a mechanism for preventing said container from separating from said drill.

32. The system of claim 31, wherein said mechanism for preventing said container from separating from said drill comprises a shoulder formed between said drill member and said shank and being situated in an interior of said container, said shoulder having a position abutting against said container to thereby prevent separation of said container from said drill.

33. A method of removing and collecting bone fragments from a donor bone site, comprising:
providing a rotatable drill having a shank engageable with a surgical rotational handpiece, said rotatable drill having a cutting member portion;
providing a container having an opening through which said cutting member passes, and having an enclosure for receiving bone fragments, said container including an inner sleeve unit and an outer sleeve surrounding at least a part of said inner sleeve unit;
urging said container against a surface of a bone at the donor bone site;
operating said handpiece so as to rotate said drill and pressing said drill in a direction to cause the drill to drill into bone at the donor bone site;
preventing rotation of said outer sleeve relative to said drill during rotation of said drill;
non-rotatably fixing said outer sleeve to said inner sleeve unit to prevent any rotation of said inner sleeve unit relative to said outer sleeve while said outer sleeve surrounds said inner sleeve unit; and
passing bone fragments created by operation of said drill at the donor bone site over said cutting member and through said opening into said container.

34. The method according to claim 33, wherein said cutting member comprises a drill bit having flutes, and wherein said bone fragments pass into said container through said flutes of said drill bit.

35. A method for removing and collecting bone fragments from a donor bone site, comprising:
providing a rotatable drill having a shank engageable with a surgical rotational handpiece, said rotatable drill having a cutting member portion;
providing a container having an opening through which said cutting member passes, and having an enclosure for receiving bone fragments;
urging said container against a surface of a bone at the donor bone site;
operating said handpiece so as to rotate said drill and pressing said drill in a direction to cause the drill to drill into bone at the donor bone site;

holding said container against rotation relative to said drill during rotation of said drill; and passing bone fragments created by operation of said drill at the donor bone site over said cutting member and through said opening into said container, said step of urging said container against a surface of the bone comprising applying an urging force to said container by a spring member during pressing of said cutting member to drill into said bone.

36. A bone grafter attachment unit for removing and collecting bone fragments from a bone, using a surgical rotational handpiece, the bone grafter attachment unit comprising:
   a rotatable drill having a shank engageable with the handpiece, and a cutting member;
   a container for receiving bone fragments and having an opening through which said cutting member passes, said container being held against rotation during rotation of said drill and said drill being movable relative to said container; and
   a rotation preventing mechanism arranged on said container for preventing rotation of at least part of said container upon rotation of said drill.

37. The bone grafter attachment unit of claim 36, wherein said rotation preventing mechanism comprises an arm attached to said container and adapted to engage the handpiece.

38. A bone grafter attachment unit for removing and collecting bone fragments from a bone, using a surgical rotational handpiece, the bone grafter attachment unit comprising:
   a rotatable drill having a shank engageable with the handpiece, and a cutting member; and
   a container for receiving bone fragments and having an opening through which said cutting member passes, said container being held against rotation during rotation of said drill and said drill being movable relative to said container, said container comprising an inner sleeve unit and an outer sleeve surrounding at least a part of said inner sleeve unit,
   said container including an engagement mechanism for engaging said inner sleeve unit and said outer sleeve together to prevent relative rotation between said inner sleeve unit and said outer sleeve while said outer sleeve surrounds said inner sleeve unit.

39. A bone grafter attachment unit for removing and collecting bone fragments from a bone, using a surgical rotational handpiece, the bone grafter attachment unit comprising:
   a rotatable drill having a shank engageable with the handpiece, and a cutting member;
   a container for receiving bone fragments and having an opening through which said cutting member passes, said container being held against rotation during rotation of said drill and said drill being movable relative to said container; and
   a pressing unit for urging said container to cover said cutting member.

* * * * *